United States Patent [19]

Van Ness et al.

[11] Patent Number: 5,130,423

[45] Date of Patent: Jul. 14, 1992

[54] NON-CORROSIVE COMPOSITIONS AND METHODS USEFUL FOR THE EXTRACTION OF NUCLEIC ACIDS

[75] Inventors: Jeffrey Van Ness, Bothell, Wash.; B. Melina Cimler, Portland, Oreg.; Rich B. Meyer, Jr.; Nicolaas M. J. Vermeulen, both of Woodinville, Wash.

[73] Assignee: MicroProbe Corporation, Bothell, Wash.

[21] Appl. No.: 649,389

[22] Filed: Feb. 1, 1991

Related U.S. Application Data

[63] Continuation-in-part of Ser. No. 552,745, Jul. 13, 1990, abandoned.

[51] Int. Cl.$^5$ .............................................. C07H 21/00
[52] U.S. Cl. ........................................ 536/27; 935/19; 935/20; 935/21; 436/175; 436/177
[58] Field of Search .................... 435/6, 268, 269, 270, 435/803; 536/27, 28, 29; 935/19; 436/11, 174, 175, 177; 514/730

[56] References Cited

U.S. PATENT DOCUMENTS 4,440,778 4/1984 Matsui et al. ........................ 514/420

OTHER PUBLICATIONS

Kirby, K. S. (1956) "A New Method for the Isolation of Ribonucleic Acids from Mammalian Tissues", Biochem. J. 64 405-408.

Kirby, K. S. (1957) "A New Method for the Isolation of Deoxyribonucleic Acids: Evidence on the Nature of Bonds between Deoxyribonucleic Acid & Protein", Biochem. J 66:495-504.

*Primary Examiner*—Robert A. Wax
*Assistant Examiner*—G. Bugaisky
*Attorney, Agent, or Firm*—Debra Leith

[57] ABSTRACT

This invention relates to safe and effective methods for the extraction of nucleic acids. In particular, methods are described for isolating nucleic acid from a sample containing a biological mixture of nucleic acids and other biological compounds wherein the sample is combined with an extraction solution containing at least one organic compound such as benzyl alcohol or a benzyl alcohol derivative to form an aqueous and non-aqueous phase. The nucleic acid is isolated from the aqueous phase. Preferably, the resulting combined solution also contains bentonite, as defined below. Typically, the sample will first be combined with a lysing agent before extraction. The lysing agents preferred are chaotropic salts such as guanidinium hydrochloride and guanidinium isothiocyanate.

13 Claims, 1 Drawing Sheet

NON-CORROSIVE COMPOSITIONS AND METHODS USEFUL FOR THE EXTRACTION OF NUCLEIC ACIDS

This invention was made with government support under Research Grant N43 AI-95021 awarded by the National Institutes of Health. The government has certain rights in the invention.

This application is a continuation-in-part of U.S. Ser. No. 07/552,745, filed on Jul. 13, 1990 now abandoned.

BACKGROUND OF THE INVENTION

1. Field of the Invention

This invention relates to compositions and assay methods for the extraction and hybridization of nucleic acids. In particular, this invention relates to compositions and methods to extract nucleic acids from cells in complex biological samples or specimens without the use of toxic compounds, such as phenol and/or chloroform, primarily through the use of benzyl alcohol or benzyl alcohol derivatives. The novel compositions and methods described here are very effective in the extraction and purification of nucleic acids.

2. Brief Description of the Relevant Art

Organic solvents such as phenol and chloroform are traditionally used in techniques employed to isolate nucleic acid from procaryotic and eucaryotic cells or from complex biological samples. Nucleic acid isolations typically begin with an enzymatic digest performed with proteases followed by cell lysis using ionic detergents, and then extraction with phenol or a phenol/chloroform combination. The organic and aqueous phases are separated and nucleic acid which has partitioned into the aqueous phase is recovered by precipitation with alcohol. However, phenol or a phenol/chloroform mixture is corrosive to human skin and is considered as hazardous waste, which must be carefully handled and properly discarded. Further, the extraction method is time consuming and laborious. Marmur, *J. Mol. Biol.* 3:208-218 (1961), describes the standard preparative procedure for extraction and purification of intact high molecular weight DNA from procaryotic organisms using enzymatic treatment, addition of a detergent, and the use of an organic solvent such as phenol or phenol/chloroform. Chirgwin et al., *Biochemistry* 18:5294-5299 (1979) described the isolation of intact RNA from tissues enriched in ribonuclease by homogenization in guanidinium thiocyanate and 2-mercaptoethanol, followed by ethanol precipitation or by sedimentation through cesium chloride.

Further, the use of chaotropic agents such as guanidinium thiocyanate (GnSCN) are widely used to lyse and release nucleic acid from cells into solution, largely due to the fact that chaotropic salts inhibit nucleases and proteases. However, it has proved difficult to isolate the nucleic acids from these chaotropic salt solutions due to the incompatibility of the chaotropes with ionic detergents and the inability to easily partition the nucleic acid into an aqueous phase, given the use of such high molar concentrations of salt.

The ability to effectively inhibit nucleases during nucleic acid isolation procedures is paramount, especially when the starting material is complex, such as feces or blood. In 1959, Brownhill et al. reported that bentonite was an inhibitor of nucleases (Brownhill et al., *Biochem. J.* 73:434 (1959)). Fraenkel-Conrat et al. later developed a procedure for the use of bentonite to inhibit ribonuclease in a procedure to purify tobacco mosaic virus (Fraenkel-Conrat et al., *Virology* 14:54-58 (1961)). Subsequent researchers reported the use of bentonite in combination with phenol and chloroform in the reduction of ribonuclease activity during the isolation of RNA (Jacoli et al., *Can. J. Biochem.* 51:1558-1565 (1973); Griffin et al., *Anal. Biochem.* 87:506-520 (1978); Grady et al., *Anal. Biochem.* 101:118-122 (1980)). It has also been reported that DNase 1 and α-amylase can be made RNAse-free by treatment with bentonite (Garrett et al., *Anal. Biochem.* 52:342-348 (1973)).

All of the above traditional nucleic acid extraction procedures, thus, require the use of toxic compounds such as phenol and/or chloroform. Researchers have long sought safer effective extraction procedures.

SUMMARY OF THE INVENTION

This invention relates to safe and effective methods for the extraction of nucleic acids. In particular, methods are described for isolating nucleic acid from a sample containing a mixture of nucleic acids and other biological compounds, wherein the sample is combined with an extraction solution containing at least one organic compound, such as benzyl alcohol or a benzyl alcohol derivative, forming an aqueous and non-aqueous phase. The nucleic acid is isolated from the aqueous phase. Preferably, the resulting combined solution also contains bentonite or Macaloid, as defined below. Typically, the sample will first be combined with a lysing agent before extraction. The lysing agents preferred are chaotropic salts, such as guanidinium hydrochloride (GuHCl) and guanidinium isothiocyanate (GuSCN).

The extraction solution described above may also advantageously be combined with a lactam, such as cyclohexylpyrrolidone, dodecylpyrrolidone, hydroxyethylpyrrolidone, octylpyrrolidone, 1-phenyl-2-pyrrolidone, and 1,3-dimethyl-3,4,5,6-tetrahydro-2-(H)-pyrrolidone.

Once the nucleic acid is separated into the aqueous phase, it can be precipitated with an alcohol, preferably ethanol or isopropanol, or concentrated with butanol. The aqueous phase can also be used directly in hybridization assays or immobilized on solid supports for subsequent probing.

The organic compounds used in the present invention are of a very low order toxicity and are not corrosive to human tissue. They retain most of the solvent properties of phenol or phenol/chloroform, and are uniquely suited to the application of nucleic acid isolation and/or fractionation of biological macromolecular complexes. In addition, they are substantially less expensive than the commonly employed organic solvents. Extraction by cesium chloride, centrifugation and alcohol precipitation may also be avoided through the use of the methods of the present invention, thus eliminating exposure to cesium chloride which is toxic. The extraction methods of the present invention are faster, simpler, safer and more sensitive than methods previously used in the extraction of nucleic acid. Thus, they represent a significant advance in the field, providing a safer means for scaling up the extraction of desired nucleic acids.

Chaotropic agents are commonly used as lysing agents in the extraction process. Due to the incompatibility of chaotropic agents with ionic detergents, it has proved difficult to isolate nucleic acids from chaotropic salt solutions. Further, it has been difficult to partition the nucleic acid into an aqueous phase, given the use of such high molar concentrations of salt. The use of bentonite in combination with the extraction solutions of the subject invention in extraction techniques involving chaotropic salts allows the rapid and simple recovery of intact RNA, DNA, or total nucleic acid from particularly complex biological samples.

DETAILED DESCRIPTION

Figure 1:
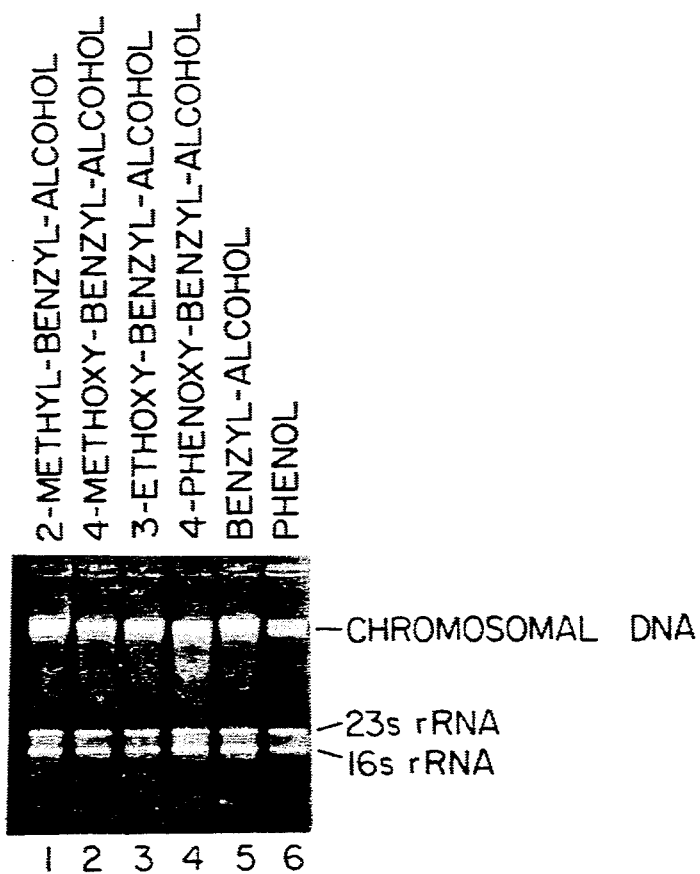
FIG. 1 shows the electrophoretic profile of total nucleic acids (chromosomal DNA and RNA) extracted using as the organic phase: 2-methyl-benzyl alcohol in lane 1; 4-methoxy-benzyl alcohol in lane 2; 3-ethoxy-benzyl alcohol in lane 3; 4-phenoxy-benzyl alcohol in lane 4; benzyl-alcohol in lane 5; and phenol in lane 6.

This invention relates to novel compositions and methods for the isolation of nucleic acid from a sample containing a biological mixture of nucleic acids and other biological compounds. The methods of the present invention enable one to easily process a biological sample containing nucleic acids by extracting nucleic acids without the use of toxic or corrosive chemicals. The methods of the present invention further enable one to prepare a nucleic acid sample for hybridization assays.

The extraction methods include combining the sample with an extraction solution containing at least one organic compound, as specified below, to form an aqueous and non-aqueous phase, and separating the aqueous phase from the non-aqueous phase. The extraction solution allows the sample to become biphasic. The nucleic acid is then isolated in the aqueous phase.

The extraction methods of the present invention may be applied to a sample containing a biological mixture of nucleic acids (ribonucleic acid (RNA) and/or deoxyribonucleic acid (DNA)) and other biological compounds which are not nucleic acids. Such a sample may include any aqueous mixture of biological material which contains nucleic acids, including complex biological mixtures of any eucaryotic and/or procaryotic cells, including protoplasts, or other biological materials which may harbor nucleic acids. The methods are thus applicable to tissue culture animal cells, animal tissue (e.g., heart, liver or brain, homogenized in lysis buffer), feces, blood cells, reticulocytes, lymphocytes, plant cells or other cells sensitive to osmotic shock, and cells of bacteria, yeasts, viruses, mycoplasmas, protozoa, rickettsia, fungi and other small microbial cells and the like.

The nucleic acid sample to be assayed or to serve as a source for the extraction of nucleic acids is combined with an extraction solution which allows for the separation of the nucleic acids in the sample from the other biological components resident in the sample. The extraction solutions comprise benzyl alcohol, derivatives of benzyl alcohol or other solvents with similar properties. The solvent must effectively cause the nucleic acids to be isolated from other biological components by partitioning the nucleic acids into an aqueous phase upon mixing the extraction solution with an aqueous sample. The extraction solution will typically comprise an organic composition having an organic compound with the following properties:

(a) a dielectric constant of about 9.0 to about 15.5;

(b) a dipole moment of about 1.35 to about 1.70 coulomb-meter; and (c) a partition coefficient of about 0.001 to about 0.3 parts water to 1 part of the organic compound. Preferably such organic compound will also have a density of about 0.7 to about 1.9 mg/ml, preferably about 1.01 to 1.9, most preferably about 1.09 to about 1.9, and will be non-corrosive to human skin. Examples of organic compounds suitable for the extraction solution are 4-hexylresorcinol and resorcinol, as well as those listed below.

The term "dielectric constant" (D), is a dimensionless number in the context of Coulomb's law:

$$F = \frac{1}{D} \cdot \frac{q1\,q2}{d^2}$$

where F is the force of attraction or repulsion, q1 and q2 are magnitudes of two electric charges separated by a distance d. A vacuum has a value 1.0 for D. Examples of other values for D are 1.00059 for air at 1 ATM and 0° C., 24.3 for alcohol at 25° C. and 80.37 for water at 20° C.

The term "dipole moment" refers to a molecular constant ($p$ or $\mu$) indicating the distribution of electrical charges in a neutral molecule or the magnitude of the + or − charge times the distance between the charge centers. One coulomb-meter = $2.99793 \times 10^{29}$ debye. It is zero, for example, if they are symmetrically distributed.

The term "partition coefficient" represents the concentration of water in the organic phase upon phase separation of equal volumes of organic solvent and water.

The extraction solution alternatively preferably comprises at least one organic compound of formula I, wherein formula I is selected from the group of compounds having the formula $C_6H_5CH_2OH$ or:

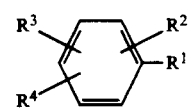

where:

$R^1$ is a member selected from the group consisting of —$(CH_2)_n$OH, in which n is 1 to 6; —CH(OH)CH$_2$OH; —CH$_2$CH(OH)CH$_2$OH and —CH(OH)COOR$^5$, in which R$^5$ is —$(CH_2)_p$CH$_3$, and in which p is 0 to 3;

$R^2$ is a member selected from the group consisting of —H; —F; —Cl; —Br; —I; —OH; —S$(CH_2)_r$CH$_3$, in which r is 0 to 3; —O$(CH_2)_q$CH$_3$, in which q is 0 to 6; —COOR$^6$, in which R$^6$ is —$(CH_2)_s$CH$_3$, and in which s is 0 to 3; —C$_6$H$_5$; —CH$_2$C$_6$H$_5$; —OC$_6$H$_5$; —OCH$_2$C$_6$H$_5$; —CH$_2$OH; —CF$_3$; and —$(CH_2)_t$CH$_3$, in which t is 0 to 6;

$R^3$ is a member selected from the group consisting of —H; —F; —Cl; —Br; —I; —OH; —CH$_3$; —$(CH_2)_x$CH$_3$, in which x is 0 to 3; —O$(CH_2)_v$CH$_3$, in which v is 0 to 3; and $R^4$ is a member selected from the group consisting of —H; —F; —Cl; —Br; —I; —$(CH_2)_yCH_3$, in which y is 0 to 3; —$O(CH_2)_wCH_3$, in which w is 0 to 3; and further, wherein $R^2$, $R^3$ and $R^4$ may occur in any position in relation to $R^1$, provided that:

(a) when $R^1$ is —CH(OH)CH$_2$OH, —CH$_2$CH(OH)CH$_2$OH or —CH(OH)COOR$^6$, then $R^2$, $R^3$ and $R^4$ must be —H;

(b) when $R^1$ is —CH$_2$OH and $R^2$ is —C$_6$H$_5$, —OCH$_2$C$_6$H$_5$, or —CH$_2$C$_6$H$_5$, $R^3$ must be —CH$_3$, —OH, —Cl, —Br, —F, —I, —H, —OCH$_3$ or —OCH$_3$CH$_3$, and $R^4$ must be —H; and (c) when R is —(CH$_2$)$_n$OH and n is 2 to 6, then $R^3$ and $R^4$ must both be —H.

Formula I is intended to include all isomer forms of the alkyls, both branched and unbranched. Unless otherwise stated, all number ranges are inclusive of the stated range, with the use of zero referring to the absence of the element. For example, —(CH$_2$)$_n$CH$_3$, in which n is 0 to 2, refers to the three components: —CH$_3$, —CH$_2$CH$_3$ and —CH$_2$CH$_2$CH$_3$. HC$_6$H$_5$ is a benzene ring.

The following compounds of formula I are particularly preferred:
those where:
$R^1$ is —(CH$_2$)$_n$OH, in which n is 1 to 4, and $R^2$, $R^3$ and $R^4$ are all —H;
where:
$R^1$ is —(CH$_2$)$_n$OH, in which n is 1 to 4;
$R^2$ is —(CH$_2$)$_t$CH$_3$, in which t is 0 to 4; and
$R^3$ and $R^4$ are both —H; or
where:
$R^1$ is —(CH$_2$)$_n$OH, in which n is 1 to 4;
$R^2$ is —O(CH$_2$)$_q$CH$_3$, in which q is 0 to 4; and
$R^3$ and $R^4$ are both —H.

The above compounds are all commercially available. Representative compounds may be purchased from Aldrich Chemical Company, Inc., Milwaukee, Wis., or Fluka Chemical Company, New York, N.Y.

The organic compounds or mixtures thereof designated above are those which have a density of about 0.7–1.9 g/ml, preferably greater than about 1.01, most preferably greater than about 1.09. They will also have a melting point of 37° C. or less.

The most preferred organic compounds of the extraction solution are benzyl alcohol, 2-methyl-benzyl alcohol, 4-methoxy-benzyl alcohol, 3-ethoxy-benzyl alcohol and 4-phenoxy-benzyl alcohol.

Some of the above organic compounds are not in liquid form, and may be dissolved in an appropriate solvent such as benzyl alcohol for use in the extraction solution.

Conventionally, organic solvents, such as phenol or a phenol-chloroform combination, are used to extract nucleic acid, using a phase separation. These methods may be used effectively with the extraction solutions of the present invention; however, an advantage of the methods of the present invention is that such toxic compounds and tedious extraction methods are not necessary.

The extraction solution is combined with the sample containing a biological mixture so that the combined solution becomes biphasic, with the non-nucleic acid material present in the organic phase and the nucleic acid material present in the aqueous phase. It is useful to saturate the organic phase with an appropriate buffer, typically the buffer used to dilute or suspend the sample. The combined solution is typically mixed and subjected to low speed centrifugation one or more times. Centrifugation is not necessary for the phase separation, but provides for a faster separation.

The nucleic acid in the aqueous phase is precipitated out with an alcohol such as ethanol or isopropanol, in the manner known to those skilled in the art. It may also be left in the aqueous phase, for example, for use in hybridization procedures. The aqueous phase may also be reextracted by adding fresh extraction solution.

The extraction solution will be combined with the sample such that the combined solution will typically contain about 10 to about 80%, preferably about 40 to about 60% and most preferably about 50% (volume:volume basis) of the organic composition as described above. Preferably then, the extraction solution will also contain standard buffers and detergents to promote lysing of cells. A buffer such as sodium citrate, Tris-HCl, PIPES or HEPES, preferably Tris-HCl at a concentration of about 0.01 to 0.1M, can be used. The buffer will typically also contain about 0.05 to 5% of an ionic or nonionic detergent, such as sodium dodecylsulfate (SDS) or sarkosyl (Sigma Chemical Co., St. Louis, Mo.), between 1 to 20 mM EDTA, and between about 0–250 mM salt, such as NaCl.

Also preferably resident in the extraction solution is a nuclease inhibitor, preferably an organoclay or the like, and more preferably bentonite, Macaloid®, Bentone® (a bentonite or hectorite organoclay platelet having a long chain organic compound bonded to its two faces) or the like, as well as combinations, derivatives or analogs thereof, at a concentration of about 0.1 to about 10%, preferably about 1 to about 5% (on a weight:volume basis). Bentonite is intended to encompass here any clay or silicate, such as diatomaceous earth, or any substance consisting primarily of montmorillonite (Al$_2$O$_3$·4SiO$_2$·H$_2$O), and typically aluminum silicate or the like. To use, the bentonite is first water-saturated and added to the extraction solution. Macaloid® (a clay) and Bentone® are available from N.L. Chemicals, Hightstown, N.J. Bentone® is particularly suitable for use within the present invention because the particulate matter remains in relatively homogeneous suspension for extended periods of time, as compared to bentonite and Macaloid®. It may be necessary to first purify the nuclease inhibitor, for instance bentonite or Macaloid®, as described in Sambrook et al., *Molecular Cloning—A Laboratory Manual*, Cold Spring Harbor Laboratory, Cold Spring Harbor, N.Y. (1989), which is incorporated by reference herein. For efficient extraction, it is preferred that small uniform particles be used. Such nuclease inhibitors are particularly desirable when extraction of RNA is desired. In samples where ribonuclease does not substantially hinder extraction, or if DNA only is being extracted, nucleic acid may be extracted without the use of such nuclease inhibitors.

The extraction solution optionally includes an aminotriarylmethane dye, such as those described in R. D. Lillie, *H. J. Conn's Biological Stains*, Williams & Wilkins, Baltimore, Md. (1977). Properties of suitable dyes include solubility in organic solvents, minimal or no partitioning into water, and minimal or no binding to nucleic acids. A preferred dye is methyl violet, with methyl violet 6B particularly preferred. The inclusion of dye in the extraction solution results in a colored organic phase and a colorless aqueous phase, thereby provided enhanced delineation of the two phases during the extraction process. The dye concentration is sufficient to provide visual contrast between the aqueous and organic phases, and typically is in the range of about 0.0005–0.01% (w/v). Because the dye is resident in the organic phase, the preferred organic compound may vary with choice of dye.

The biological samples are typically lysed through the use of lysing agents, prior to or during extraction, to disturb the protein structure and to release the nucleic acid. Preferably, the sample will be subjected to lysis prior to the addition of the extraction solution. Any lysing agents typically used in nucleic acid extraction procedures are appropriate, such as SDS, lysozyme, Proteinase K in various combinations with chaotropic agents, or any other agent which would weaken or disrupt the integrity of the cell membrane.

Chaotropic agents, which disturb the secondary and tertiary structure of proteins (for example, guanidinium salts such as guanidinium hydrochloride (GuHCl), guanidinium isothiocyanate (GuSCN), urea or other isothiocyanates), may be used as lysing agents, in combination with or prior to the extraction solution, to dissociate nucleic acids and inhibit nucleases. The use of chaotropic agents in the extraction and hybridization of nucleic acids is described in E.P Publication No. 0 127 327, which is incorporated by reference herein. The chaotropic agent is present at a concentration sufficient to release nucleic acid from target cells and to protect the released nucleic acid from nucleases. Typically, the chaotrope is present at a concentration from about 1M to about 5M, and more preferably is present at about 2M to about 3M. Lactams may also be used in combination with the extraction solution to facilitate lysing and extraction. Examples of lactams and their use in extraction procedures are thoroughly described in commonly assigned U.S. Ser. No. 07/384,235, filed on Jul. 24, 1989, which is incorporated by reference herein. Preferred lactams are cyclohexylpyrrolidone, 1-phenyl-2-pyrrolidone and 1,3-dimethyl-3,4,5,6-tetrahydro-2-(H)-pyrrolidone.

For the extraction of total nucleic acid (DNA and RNA), extraction typically takes place at about 37° C. to about 65° C. for about 1 to 10 minutes. The extraction procedure will preferably yield an aqueous sample having a concentration of nucleic acid such that after combining the sample with the extraction solution, the amount of nucleic acid present in the aqueous phase will not be in excess of 1 mg/ml. A useful rule of thumb is to not permit the total biological material to exceed 50 mg/ml in a given sample. The ratio of sample volume to extraction solution volume is typically 0.5:1 to 3:1, more typically 0.75:1 to 2:1, most typically about 1:1.

EXTRACTION OF RIBOSOMAL RNA

Extraction solutions of the present invention also permit the selective extraction of ribosomal RNA (rRNA). After the sample containing the nucleic acids has been lysed, the sample is heated prior to or after combining the sample with the extraction solution. The yield of rRNA is increased 5 to 50 fold by heating the sample at about 65° C. for about 10 minutes before or after addition of the extraction solution. If no heat is used, DNA is primarily extracted.

Thus, a sequential extraction of rRNA and DNA may be accomplished by first lysing the sample. Then, extraction is performed at room temperature using the extraction solutions as described herein, and DNA is isolated from the first aqueous phase, the rRNA remaining in the first organic phase. The rRNA is then extracted from the first organic phase after the addition of a standard buffer solution (e.g., 1% SDS, 50 mM Tris, 25 mM EDTA and 0.05 mM NaCl). This solution is heated, typically to about 65° C., to create a second organic phase and second aqueous phase.

Extraction solutions which are most preferred and which may be alternatively offered in kit form are those extraction compositions which comprise bentonite or Bentone ®, a lysing agent, and an organic compound selected from those described above in connection with the extraction solutions. The novel extraction compositions may include in combination any of the elements described above, which may be included in the variously described extraction solutions.

EXTRACTION TO IMPROVE HYDRIDIZATION

It is also advantageous to use the extraction methods and compositions of this invention prior to conducting a hybridization assay on a complex biological sample, such as on feces or blood. The extraction procedure may be necessary in some cases to remove contaminants which contribute to background interference. Extraction followed by procedures to concentrate the nucleic acid may improve sensitivity and the signal-to-noise ratio in hybridization assays.

A hybridization assay according to the present invention can be performed by any method known to those skilled in the art or that is analogous to immunoassay methodology given the guidelines presented herein. Preferred methods of assay are the sandwich assays and variations thereof, and the competition or displacement assay. Hybridization techniques are generally described in "Nucleic Acid Hybridization, A Practical Approach," Ed. Hames, B. D. and Higgins, S. J., IRL Press, 1985; Gall and Pardue (1969), *Proc. Natl. Acad. Sci. U.S.A.* 63:378–383; and John, Burnsteil and Jones (1969) *Nature* 223:582–587. As improvements are made in hybridization techniques, they can readily be applied.

Sandwich assays are commercially useful hybridization assays for detecting or isolating nucleic acid sequences. Such assays utilize a "capture" nucleic acid covalently immobilized to a solid support and labelled "signal" nucleic acid in solution. The clinical sample will provide the target nucleic acid. The "capture" nucleic acid and "signal" nucleic acid probe hybridize with the target nucleic acid to form a "sandwich" hybridization complex. To be effective, the signal nucleic acid cannot hybridize with the capture nucleic acid.

In a hybridization assay, the target nucleic acid is the nucleotide sequence of deoxyribonucleic acid (DNA), ribonucleic acid (RNA) or ribosomal ribonucleic acid (rRNA), whose presence is of interest and whose presence or absence is to be detected. The target nucleic acid may be provided in a complex biological mixture of nucleic acid (RNA, DNA and/or rRNA) and non-nucleic acid.

The hybridization media may be pre-prepared, either commercially or in the laboratory, to contain all the necessary components for hybridization. For instance, in a sandwich assay the media could comprise a lactam, desired buffers and detergents, a capture nucleic acid bound to a solid support such as a microbead, and a signal nucleic acid. This media then need only be combined with the solution containing the target nucleic acid at the time the assay is to be performed. Once hybridization occurs, the hybridization complex attached to the solid support may be washed and the extent of hybridization determined.

Once the appropriate sequences are determined, DNA probes are preferably chemically synthesized using commercially available methods and equipment. For example, the solid phase phosphoramidite method can be used to produce short probes of between 15 and 50 bases and having a molecular weight of less than 16,000 daltons. (Caruthers et al., *Cold Spring Harbor Symp. Quant. Biol.* 47:411–418 (1982), and Adams et al., *J. Am. Chem. Soc.* 105:661 (1983)). When synthesizing a probe for a specific target, the choice of nucleotide sequence will determine the specificity of the test. For example, by comparing DNA sequences from several virus isolates, one can select a sequence for virus detection that is either type specific or genus specific. Comparisons of DNA regions and sequences can be achieved using commercially available computer programs.

The determination of the extent of hybridization may be done by any of the methods well-known in the art. If there is no detectable hybridization, the extent of hybridization is thus 0. Typically, labelled signal nucleic acids are used to detect hybridization. Complementary nucleic acids or signal nucleic acids may be labelled by any one of several methods typically used to detect the presence of hybridized polynucleotides. The most common method of detection is the use of autoradiography with $^3H$, $^{125}I$, $^{35}S$, $^{14}C$, or $^{32}P$ labelled probes or the like. The choice of radioactive isotope depends on research preferences due to ease of synthesis, varying stability, and half lives of the selected isotopes. Other labels include ligands which bind to labelled antibodies, fluorophores, chemiluminescent agents, enzymes, and antibodies which can serve as specific binding pair members for a labelled ligand. The choice of label depends on sensitivity required, ease of conjugation with the probe, stability requirements, and available instrumentation.

Kits for the extraction of and hybridization of nucleic acids are also contemplated, which comprise the above solutions and compositions in various desired combinations.

Typically, compounds present in biological samples exert an inhibitory effect on target amplification procedures, such as PCR and LCR. This observed inhibition is particularly problematic with amplification of nucleic acid extracted from blood samples. The methods of the present invention remove most, if not all, inhibitors of target amplification from biological samples in general, and particularly from blood. Thus, the claimed methods may be advantageously used in combination with target amplification procedures. The present invention is particularly suited to target amplification of nucleic acid obtained from biological samples containing low copy number target nucleic acid.

The following examples are offered by way of illustration and are not to be construed as limiting the invention, as claimed, in any way.

EXAMPLES

EXAMPLE 1

Extraction of total nucleic acids with benzyl alcohol and benzyl alcohol derivatives This extraction protocol allows the isolation of nucleic acids from samples lysed with guanidinium isothiocyanate without the use of phenol or phenol/chloroform. The organic phase is composed of benzyl alcohol or a derivative of benzyl alcohol.

Approximately $5 \times 10^9$ *Bacteroides gingivalis* cells were lysed in 750 µl of 3M GuSCN (Kodak, Rochester, N.Y.) lysing solution containing 2% sarkosyl (Sigma Chemical Company, St. Louis, Mo.), 50 mM Tris (pH 7.6), and 25 mM EDTA. Then 100 µl of the lysate was aliquoted equally into 6-1.5 ml microcentrifuge tubes. To each tube was added respectively: 500 µl of organic phase saturated with 0.05M Tris-HCl, 5 mM EDTA (pH 7.2), where the organic phase in:

tube 1 was 2-methyl-benzyl alcohol (Aldrich Chemical Company, Milwaukee, Wis.);
tube 2 was 4-methoxy-benzyl alcohol (Aldrich);
tube 3 was 3-ethoxy-benzyl alcohol (Aldrich);
tube 4 was 4-phenoxy-benzyl alcohol (Aldrich);
tube 5 was benzyl alcohol (Aldrich); and
tube 6 was phenol (Bethesda Research Laboratories (BRL), Gaithersburg, Md.);

and 250 µl of extraction buffer (0.05M NaCl, 50 mM Tris-HCl (pH 7.2), 5 mM EDTA and 0.5% sodium dodecyl sulfate (Sigma Chemical Company, St. Louis, Mo. (SDS)). The solutions were vigorously mixed for 15 seconds and heated at 65° C. for 10 minutes. The tubes were then again vigorously mixed for 15 seconds. The phases were then separated by centrifugation at 10,000 rpm in a microcentrifuge. The upper aqueous phase was removed (generally a volume of 400 µl) and then twice the volume of 100% ethanol was added to the aqueous phase. Precipitation of the nucleic acid was allowed to occur for 5 minutes at 19° C. The nucleic acids were then pelleted from solution by centrifugation at 10,000 rpm for 10 minutes. The liquid phase was then decanted and discarded. The nucleic acid pellet was dissolved in 100 µl of distilled water and then subjected to agarose gel electrophoresis. The results are presented in FIG. 1, and indicate that the extractions were all comparable in yield and purity to those using phenol.

EXAMPLE 2

Extraction of total nucleic acids from fecal samples using benzyl alcohol and bentonite This extraction protocol allows the isolation of nucleic acids from particularly complex samples lysed with guanidinium isothiocyanate without the use of phenol or phenol/chloroform. The organic phase is composed of benzyl alcohol and bentonite.

Fecal samples in transport medium (Trend Fekal ™ Enteric Plus Transport System, Trend Scientific Inc., St. Paul, Minn.) were aliquoted into 100 µl portions. Each aliquot was lysed with 300 µl of GuSCN lysis solution, as in Example 1, and were spiked with $5 \times 10^8$ *Bacteriodes gingivalis* cells. Following spiking, the samples were divided into two equal sets. One set was extracted using phenol, and the other set was extracted by adding 500 µl of a benzyl alcohol/bentonite solution which comprised: benzyl alcohol, containing 1% W/V $H_2O$-saturated bentonite (Sigma) and 250 µl of extraction buffer (0.05M NaCl, 50 mM Tris-HCl (pH 7.2), 5 mM EDTA and 0.5% sodium dodecyl sulfate). The solutions were vigorously mixed for 15 seconds and heated at 65° C. for 10 minutes. The tubes were then again vigorously mixed for 15 seconds. The phases were then separated by centrifugation at 10,000 rpm for 2 minutes in a microcentrifuge. The upper aqueous phase was removed (generally a volume of 400 µl) and then twice the volume of 100% ethanol was added to the aqueous phase. Precipitation of the nucleic acid was allowed to occur for 5 minutes at 19° C. The nucleic acids were then pelleted from solution by centrifugation at 10,000 rpm for 10 minutes. The liquid phase was then decanted and discarded. The nucleic acid pellet was dissolved in 100 μl of distilled water and then subjected to agarose gel electrophoresis.

Figure 2:
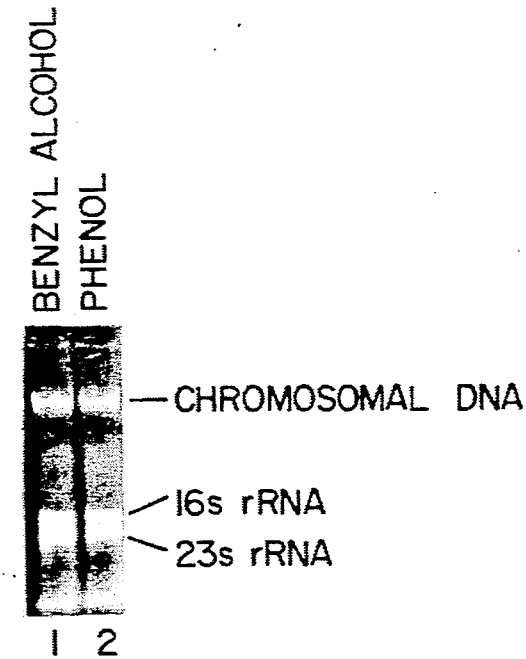
FIG. 2 shows the electrophoretic profile of total nucleic acids from extracted fecal samples using benzyl alcohol and bentonite. In lane 1 is shown the electrophoretic profile of total nucleic acids isolated from fecal samples spiked with bacteria (*Bacteroides gingivalis*) when the extraction solution is composed of benzyl alcohol and 1% W/V bentonite. In comparison, lane 2 shows the profile when the extraction solution is composed of phenol. In both extractions, the recovery of total nucleic acids is comparable, and 16S and 23S rRNAs are isolated in the intact form.

For the phenol extraction, samples were lysed as above and extracted exactly as described for the benzyl alcohol procedure. The phases were separated by centrifugation as above, and the aqueous phase re-extracted at 65° C. with an additional volume of phenol. The isolated nucleic acids were then precipitated with 70% ethanol, as above. The liquid phase was decanted and discarded. The nucleic acid pellet was dissolved in 100 μl of distilled water and then subjected to agarose gel electrophoresis. The results are presented in FIG. 2, which shows that total nucleic acids may be isolated from sources with high nuclease levels using the benzyl alcohol extraction.

EXAMPLE 3

Improved hybridization procedures by pre-extraction of a complex biological sample The assay utilizes nylon solid supports in a sandwich assay format in which a target nucleic acid sequence is sequestered and then detected using a fluorescence-based assay format.

Fecal samples in transport medium (Trend Fekal ™ Enteric Plus Transport System, Trend Scientific Inc.) were aliquoted into 100 μl portions. Each aliquot was lysed with 300 μl of GuSCN lysis solution as in Example 1, and was spiked with $5 \times 10^8$ *Bacteroides gingivalis*. Following spiking, the samples were divided into two equal aliquots. One aliquot was extracted using the benzyl alcohol/bentonite method, as described above in Example 2, and the other aliquot was not subjected to extraction. The nucleic acid pellet from the extracted sample was dissolved into 100 μl of 3M GuSCN lysis solution (in 2% sarkosyl, 50 mM Tris (pH 7.6) and 25 mM EDTA). Both the unextracted lysate and the isolated nucleic acid in 3M GuSCN were heated to 65° C. for 5 minutes. A biotinylated 24-mer oligonucleotide probe complementary to conserved regions of bacterial 16S rRNA (signal probe) was added to a final concentration of 100 nanograms per ml to the lysate and to the isolated nucleic acid.

5-fold serial dilutions of the lysates were made using diluents in the 3M GuSCN lysing solution containing the biotinylated signal oligonucleotides:

Oligonucleotide sequences:

Bg1: 5'-XCAATACTCGTATCGCCCGTTATTC-3'

UP9A: 5'-XCTGCTGCCTCCCGTAGGAGT-3' and $1 \times 10^8$ total cells of *Actinobacillus actinomycetecomitans*, *Bacteroides intermedius*, *Eikenella corrodens*, *Wolinella recta*, and *Fusobacterium nucleatum* in the case of the extracted sample and the fecal lysate in the case of the unextracted sample. The diluents contained 100 mg/ml biotinylated signal oligonucleotide, as described above. The solutions were then incubated for 30 minutes at ambient temperature with 2 nylon beads prepared by The Hoover Group (Sault St. Marie, Mich.) that had covalently immobilized 0.1 μg of Bg1-specific oligonucleotide probe (capture probe). The solid supports were washed with SDS/FW (0.09M NaCl, 50 mM Tris pH 7.6, 25 mM EDTA and 0.1% SDS) at ambient temperature, following by washing with 0.5% Tween 20® (Pierce, Rockford, Ill.), 1 mM MgCl₂, 0.01M Tris-HCl pH 8.0 (APB), and then incubated with 0.4 μg/ml of streptavidin/alkaline phosphatase (SA/AP) conjugate in APB for 5 minutes at ambient temperature. The solid supports were then washed 5 times with APB, TMNZ (0.05M Tris (pH 9.5), 1 mM MgCl₂, 0.5 mM ZnCl₂), and then the presence of alkaline phosphatase was determined by incubating the nylon beads with 150 μl of 0.5 mM 4-methyl-umbelliferyl phosphate (4-hydroxymethyl coumarin) in black microtiter well strips (Dynatek Laboratories, Chantilly, Va.). Incubation was for 30 minutes at 37° C. The solution was then decanted and placed in a 96 well microtiter plate. The plates were then directly read using a Fluoroskan II fluorometer (Flow Laboratories, McLean, Va.) using an excitation wavelength of 360 nm and an emission wavelength of 456 nm. The results are shown in Table 1 below.

TABLE 1

| Cell number: | Fluorescent Signal | |
|---|---|---|
| | Extracted sample | Non-Extracted Sample |
| $1 \times 10^8$ | 1876 | 2100 |
| $2 \times 10^7$ | 1350 | 2100 |
| $4 \times 10^6$ | 740 | 1550** |
| $8 \times 10^5$ | 220 | 1180 |
| $1.6 \times 10^5$ | 56 | 980 |
| $3.2 \times 10^4$ | 29 | 1210 |
| $6.4 \times 10^3$ | 23** | 1160 |
| control | 18 | 940 | where ** indicates the lowest level of detection.

The results indicate that, in the 30 minute hybridization, a level of $6 \times 10^3$ cells was detected using the extracted sample, whereas with the unextracted sample a level of only $4 \times 10^6$ cells were detected.

EXAMPLE 4

Extraction of DNA from biological samples using benzyl alcohol and Bentone ®

A suspension of *E. coli* was harvested by centrifugation, and the pellet was resuspended to between $10^8$ and $10^{10}$ cells/ml in 50 mM Tris buffer (pH 7.6) containing 10 mM EDTA and 10% (w/v) sucrose. The suspension was then incubated for 5–15 minutes at ambient temperature. Alternatively, a blood sample was collected in a collection tube containing sodium EDTA.

The biological sample (either the bacterial suspension or the blood sample) was lysed with an equal volume of lysis buffer (5M GuSCN, 83 mM Tris-HCl, pH 7.6, 17 mM EDTA and 3.3% (w/v) sarkosyl).

The lysate (200 μl) was transferred to a 2 ml microcentrifuge tube. After vigorous shaking, 700 μl of an extraction solution (1.1% (w/v) Bentone® in 99% pure benzyl alcohol) was added to the lysate. To this mixture was added 400 μl buffer (50 mM Tris-HCl, pH 7.6, 10 mM EDTA, 100 mM NaCl, 0.5% (w/v) SDS). The mixture was vortexed 10 seconds, then centrifuged at $12,000 \times g$ for 5 minutes. The upper aqueous phase was transferred to a new 2 ml microcentrifuge tube and 0.1 volume 3M sodium acetate was added. An equal volume of isopropanol was added, and the solution mixed gently to precipitate DNA. After centrifugation at $12,000 \times g$ for 10 minutes, the supernatant was discarded and 1 ml of 70% ethanol was added to the pelleted DNA. After gentle mixing, the preparation was centrifuged at $12,000 \times g$ for 5 minutes. The supernatant was discarded, the pellet was air dried, and the DNA pellet was then resuspended in RNase-free water or appropriate buffer to a desired concentration.

DNA extracted according to the protocol set forth in this Example is suitable for use in target amplification procedures, such as PCR (polymerase chain reaction). Various target amplification procedures are well known in the art. Table 2 below shows that the DNA extraction procedure of this Example permits amplification and detection of low copy number target nucleic acid. Briefly, known concentrations of an HIV-1 plasmid were added to human whole blood to give 0–250 pHIV-1 copies per PCR reaction. Duplicate 100 μl blood samples were extracted, the extracted nucleic acid was resuspended in 100 μl of water, and 50 μl of this nucleic acid suspension were used per amplification reaction. Amplified target was detected by hybridization of a complementary $^{32}$P-labeled oligonucleotide probe.

TABLE 2

| Amplification and Detection of Low Copy Number Target DNA | |
|---|---|
| pHIV-1 Copies per PCR Reaction | Signal Detected |
| 250 | + |
| 100 | + |
| 50 | + |
| 20 | + |
| 10 | + |
| 5 | + |
| 2 | − |
| 0 | − |
| Negative PCR controls | − |

Table 3 below compares extraction of DNA from whole blood using a Proteinase K/phenol extraction method versus the extraction method of this Example. Briefly, three PCR-positive HTLV-I blood samples and five control blood samples (HTLV-I negative by PCR) were collected in tubes containing sodium EDTA. Each of the positive samples was serially diluted in 5-fold steps with the control blood. Duplicate 100 μl blood samples were extracted using a Proteinase K/phenol procedure (see, for example, Sambrook et al., in "Molecular Cloning. A Laboratory Manual", Cold Spring Harbor Laboratory Press, N.Y, 1989; R. Higuchi, in "Amplifications. A Forum for PCR Users", Perkin-Elmer Corp., Norwalk, Conn., 1989) or the method of this Example. The extracted nucleic acid was resuspended in 100 μl of water, and 50 μl of this nucleic acid suspension were used per PCR reaction. Amplified target was detected by hybridization of a complementary $^{32}$P-labeled oligonucleotide probe. Table 3 demonstrates that Proteinase K/phenol and the described procedure provide comparable limits of extraction and detection.

TABLE 3

| Comparison of Proteinase K/Phenol and the Extraction Procedure of Example 4 - PCR Amplification and Detection of Nucleic Acid From Whole Blood | | |
|---|---|---|
| Dilution Factor of HTLV-I Positive Blood Sample | Signal Detected | |
|  | Proteinase K/ Phenol | Example 4 |
| 1 | + | + |
| 5 | + | + |
| 25 | + | + |
| 125 | + | + |
| 625 | − | − |
| 3125 | − | − |
| HTLV-I Negative Blood | − | − |
| Negative PCR Controls | − | − |

EXAMPLE 5

Extraction of total nucleic acid from biological samples using C, benzyl alcohol and Bentone ®

A suspension of *E. coli* was harvested by centrifugation, and the pellet was resuspended to between $10^8$ and $10^{10}$ cells/ml in 50 mM Tris buffer (pH 7.6) containing 10 mM EDTA and 10% (w/v) sucrose. The suspension was then incubated for 5–15 minutes at ambient temperature. Alternatively, a blood sample was collected in a collection tube containing sodium EDTA.

The biological sample (either the bacterial suspension or the blood sample) was lysed with an equal volume of lysis buffer (5M GuSCN, 83 mM Tris-HCl, pH 7.6, 17 mM EDTA and 3.3% (w/v) sarkosyl).

The lysate (200 μl) was transferred to a 2 ml microcentrifuge tube. After vigorous shaking, 700 μl of an extraction solution (1.1% (w/v) Bentone ® in 99% pure benzyl alcohol) was added to the lysate. To this mixture was added 400 μl buffer (50 mM Tris-HCl, pH 7.6, 10 mM EDTA, 100 mM NaCl, 0.5% (w/v) SDS). The mixture was vortexed 10 seconds, heated for 10 minutes at 65° C. with occasional mixing, and then centrifuged at 12,000×g for 5 minutes. The upper aqueous phase was transferred to a new 2 ml microcentrifuge tube, and 500 μl extraction solution (benzyl alcohol and Bentone ®, as described above) were added. The mixture was vortexed 10 seconds and centrifuged at 12,000×g for 5 minutes. The upper aqueous phase was again transferred to a new 2 ml microcentrifuge tube, and 0.1 volume 3M sodium acetate was added. An equal volume of isopropanol was added, and the solution mixed gently to precipitate total nucleic acid. After centrifugation at 12,000×g for 10 minutes, the supernatant was discarded and 1 ml of 70% ethanol was added to the pelleted nucleic acid. After gentle mixing, the preparation was centrifuged at 12,000×g for 5 minutes. The supernatant was discarded, the pellet was air dried, and the nucleic acid pellet was then resuspended in RNase-free water or appropriate buffer to a desired concentration.

What is claimed is:

1. A method for isolating nucleic acid from a sample containing a mixture of nucleic acids and other biological compounds comprising:
   combining the sample with an extraction solution containing at least one organic compound of formula I;
   forming an aqueous and non-aqueous phase; and
   separating the aqueous phase from the non-aqueous phase, wherein formula I is selected from the group of compounds having the formula $C_6H_5CH_2OH$ or:

where:
   $R^1$ is $-CH_2OH$;
   $R^2$ is a member selected from the group consisting of $-H$, $-F$, $-Cl$, $-Br$, $-I$, $-OH$, $-S(CH_2)_rCH_3$ in which r is 0 to 3, $-O(CH_2)_qCH_3$ in which q is 0 to 6, $-COOR^6$ in which $R^6$ is $-(CH_2)_sCH_3$ in which s is 0 to 3, $-C_6H_5$, $-CH_2C_6H_5$, $-OC_6H_5$, —OCH$_2$C$_6$H$_5$, —CH$_2$OH, —CF$_3$, and —(CH$_2$)$_t$CH$_3$ in which t is 0 to 6;

R$^3$ is a member selected from the group consisting of —H, —F, —Cl, —Br, —I, —OH, —CH$_3$, —(CH$_2$)$_x$CH$_3$ in which x is 0 to 3, —O(CH$_2$)$_n$CH$_3$ in which v is 0 to 3; and R$^4$ is a member selected from the group consisting of —H, —F, —Cl, —Br, —I, —(CH$_2$)$_y$CH$_3$ in which y is 0 to 3, —O(CH$_2$)$_w$CH$_3$ in which w is 0 to 3, and further, wherein R$^2$, R$^3$ and R$^4$ may occur in any position in relation to R$^1$.

2. The method of claim 1 wherein when R$^2$ is —C$_6$H$_5$, —OCH$_2$C$_6$H$_5$, or —CH$_2$C$_6$H$_5$, R$^3$ must be —CH$_3$, —OH, —Cl, —Br, —F, —I, —H, —OCH$_3$ or —OCH$_2$CH$_3$ and R$^4$ must be —H.

3. The method of claim 1 wherein the extraction solution further comprises a clay or a silicate.

4. The method of claim 3 wherein the clay or silicate is montmorillonite clay, an organic derivative of montmorillonite clay, diatomaceous earth, aluminum silicate or a combination, derivative or analog thereof.

5. The method of claim 3 wherein the clay or silicate is at a concentration of about 0.1% to about 10%.

6. The method of claim 1 wherein the sample is combined with a lysing agent before extraction.

7. The method of claim 6 wherein the lysing agent is a chaotropic agent.

8. The method of claim 6 wherein the lysing agent is selected from the group consisting of guanidinium hydrochloride, guanidinium thiocyanate, urea and combinations thereof.

9. The method of claim 1 wherein the organic compound or combination thereof is one which has a density of 1.01 g/ml or greater.

10. The method of claim 1 wherein the nucleic acid is precipitated from the aqueous phase with an alcohol.

11. The method of claim 10 wherein the alcohol is ethanol or isopropanol.

12. The method of claim 1 wherein the organic compound of formula I is selected from the group consisting of benzyl alcohol, 2-methyl-benzyl alcohol, 4-methoxy-benzyl alcohol, 3-ethoxy-benzyl alcohol, and 4-phenoxy-benzyl alcohol.

13. The method of claim 1 further comprising, after the step of combining the sample with an extraction solution, the step of heating for about 1 to about 10 minutes at about 37° to about 65° C.

* * * * *